United States Patent [19]

Jeromin et al.

[11] Patent Number: 4,698,186

[45] Date of Patent: Oct. 6, 1987

[54] PROCESS FOR THE PRE-ESTERIFICATION OF FREE FATTY ACIDS IN FATS AND OILS

[75] Inventors: Lutz Jeromin; Eberhard Peukert, both of Hilden; Gerhard Wollmann, Duesseldorf, all of Fed. Rep. of Germany

[73] Assignee: Henkel Kommanditgesellschaft auf Aktien, Duesseldorf, Fed. Rep. of Germany

[21] Appl. No.: 821,109

[22] Filed: Jan. 21, 1986

[30] Foreign Application Priority Data

Jan. 21, 1985 [DE] Fed. Rep. of Germany ....... 3501761

[51] Int. Cl.$^4$ ............................ C11C 3/04; C11C 3/10
[52] U.S. Cl. .................................... 260/421; 560/204; 560/234
[58] Field of Search ................. 260/421; 560/204, 234

[56] References Cited

U.S. PATENT DOCUMENTS

| | | | |
|---|---|---|---|
| 1,228,888 | 6/1917 | Dreymann | 260/421 |
| 1,701,703 | 2/1929 | Starrels | 260/421 |
| 2,360,844 | 10/1944 | Bradshaw et al. | 260/410.9 |
| 2,494,366 | 1/1950 | Sproles et al. | 260/410.9 |
| 2,678,332 | 5/1954 | Cottle | 560/204 |
| 3,037,052 | 5/1962 | Bortnick | 560/204 |
| 4,164,506 | 8/1979 | Kawahara et al. | 260/421 |
| 4,608,202 | 8/1986 | Lepper et al. | 560/234 |

OTHER PUBLICATIONS

Sussman, I. & E. C., vol. 78, No. 12, pp. 1228-1230, Dec. 1946,.

*Primary Examiner*—J. E. Evans
*Attorney, Agent, or Firm*—Ernest G. Szoke; Henry E. Millson, Jr.

[57] ABSTRACT

A process for reducing the free fatty acid content of fats and oils by esterifying the free fatty acids with a lower monoalcohol in the presence of an acidic cation exchange resin as a solid esterification catalyst.

11 Claims, No Drawings

PROCESS FOR THE PRE-ESTERIFICATION OF FREE FATTY ACIDS IN FATS AND OILS

BACKGROUND OF THE INVENTION

1. Field of the Invention

This invention relates to a simple process for pretreating triglycerides, especially natural fats and oils, for reducing their troublesome content of free fatty acids. The process of the present invention is particularly intended as a preparatory treatment for subsequent conversion of the triglycerides by transesterification with lower monohydric alcohols, particularly methanol, into glycerine and the corresponding fatty acid alkyl esters.

2. Description of Related Art

Fatty acid methyl esters have acquired considerably commercial significance as starting materials for the production of fatty alcohols and other oleochemical products, such as ester sulfonates, fatty acid alkanolamides and soaps. Industrially, fatty acid methyl esters are produced mainly by catalytic transesterification (alcoholysis) of fatty acid triglyceride mixtures of the type present in fats and oils of vegetable and animal origin.

Natural fats and oils almost always contain considerably quantitites of free fatty acids. their content of free fatty acids varies over a wide range, dependign on the origin of the material and its previous history, and almost always exceeds about 3% by weight.

Various processes are available for the transesterification of naturally occurring fatty acid triglycerides with alcohols. The choice of transesterification reaction conditions depends to a large extent upon the quantity of free fatty acids presesnt in the triglyceride mixture.

Atmosphere transesterification of fats and oils to form the corresponding fatty acid ester mixture may be effected with a 0.5 to 1.0-molar excess of alcohol in the presence of an alkali catalyst and at a temperature of between 25° to 100° C. Such a process is described in U.S. Pat. No. 2,360,844 as the first stage of a soap manufacturing process. This alkali-catalyzed, atmospheric transesterification process may be carried out without any problems as long as the starting materials used are fats and oils which are substantially free from water and which have a free fatty acid content ofless than 0.5% by weight (corresponding to an acid number of about 1).

Fats and oils having a relatively high content of free fatty acids may be transesterified in a high pressure transesterification process with a 7- to 8- molar excess of methanl in the presence of alkali or zinc catalysts to form the corresponding fatty acid methyl esters. This process is carried out at a temperature of 240° C. and at a pressure of about 100 bar. (Ullmann, Enzyklopadie der technischen Chemie, 4th Edition, Vol 11 (1976), page 432).

Compared with high-pressure transesterification, atmospheric transesterification uses considerably less methanol and, by virtue of the lower reaction temperatures, less energy. In addition, atmospheric transesterification does not require expensive pressure reactors.

Commercial grade fats and oils, however, almost always contain relatively large quantities of water and free fatty acids. As a result, atmospheric transesterification of these commercial triglyceride mixtures requires preliminary drying and a reduction in the acid number, for example by conversion of the free fatty acids into the corresponding alkyl or glycerol esters in a preliminary or pre-esterification reaction. Pre-esterification of the acid-containing fats and oils may be carried out in the presence of alkaline cataylsts at a temperature of 240° C. and at a pressure of 20 bar. (Ullmann, Enzyklopadie der technischen Chemie, 4th Edition, Vol. 11 (1976), page 432). This method of pre-esterification with methanol also requires the use of expensive pressure reactors.

It also is known that the free fatty acid content of oils can be esterified with lower monohydric alcohols, especially methanol, in the presence of an acid catalyst such as p-toluene sulfonic acid in a homogeneous phase reaction. Unfortunately, in order to prepare the pre-esterified product for subsequent alkali catalyzed transesterification, this process requires a relatively complicated separation of the catalyst and also the removal of water by washing the esterified oil with methanol. It is absolutely essential that the catalyst—normally p-toluene sulfonic acid—be carefully removed because any catalyst residue in the methyl ester during its subsequent reaction to form a fatty acid alcohol also can inhibit the hydrogenation catalysts. In order to separately remove the methanol wash containing the recovered water and acid catalyst, a liquid extractant which is substantially immiscible with the oil phase must be added to the oil for pre-esterification. Glycerine preferably is used as the immiscible extractant. Such a process is described in German application Pat. No. 33 19 590. Unfortunately, a portion of the esterified free fatty acids are lost in this known process.

An object of the present invention is to provide an improved process having all the advantages of the acid-catalyzed pre-esterification process, including in particular compratively mild reaction temperatures and pressures, but which avoids the difficulties involved in the reliable removal of undesirable acidic catalyst residue from the pre-esterified material.

DESCRIPTION OF THE INVENTION

According to the present invention, this and other objects are achieved by a process for reducing the level of free fatty acids present ina fat or oil comprising (a) esterifying free fatty acids in said fat or oil with a lower monoalcohol in the presence of an acidic ion exchange resin as a solid, acidic esterification catalyst and (b) separately recovering the fat or oil containing esterified free fatty acids from the solid acidic esterification catalyst.

Thus the present invention relates to the pre-esterification of fats and oils, preferably of natural origin, in a heterogeneous phase reaction using a solid acid catalyst which does not dissolve in the reaction mixture and which, as a result, may be reliably separated from the reaction product by a simple phase separation.

The pre-esterification of free fatty acids in fats and oils in accordance with the present invention using heterogeneous catalysis by employing a solid ion (cation) exchange resin combines the advantages of acid catalysis with a simple and totally reliable procedure for separating the acid catalyst from the treated material. Thus, the esterification process is considerably simplified and significant savings can be realized.

Suitable triglyceride starting materials for the process of the present invention include virtually any fats and oils of vegetable or animal origin. Of course, fats and oils having a free fatty acid content that is naturally low enough that they may be directly subjected, without and disadvantage, to alkali-catalyzed, atmospheric transesterification need not be treated using the present invention.

Possible starting materials for the present invention include, in particular, coconut oil, palm kernel oil, olive oil, rape oil, cottonseed oil, lard oil, fish oil, and beef tallow. Normally, these crude materials can be esterified directly without requiring preliminary purification. Surprisingly, the heterogeneous solid catalysts used in the present invention show very little, if any, loss of activity after prolonged periods of operation, even in continuous processing using crude fats and oils. Any loss in activity may be reclaimed by washing the solid catalyst with the monohydric alcohol used for pre-esterification, or, if necessary, by reactivating the acidic ion exchange groups in the resin.

The acid number of natural fats and oils, and hence their free fatty acid content, may vary within wide limits. For example, the acid number of commercial, crude coconut oil is generally not above 20. Other vegetable oils have acid numbers ranging from below about 10 (good qualities) to 20–25 (inferior qualities). Commercial tallows, which are valued and handled according to their acid number, have acid numbers ranging form about 1 to 40, sometimes even higher, corresponding to a free fatty acidcontent of from about 0.5 to 20% by weight. In extreme cases, thea cid number of a suitable starting material for the process of the present invention may reach a level of 60 or higher.

In the process of the present invention, free fatty acids present in the starting triglyceride mixture are esterified with a molar excess (relative to the fatty acids) of a lower monoalcohol, i.e., an alkanol having 1 to 4 carbon atoms, in the presence of a solid acidic esterification catalyst. The preferred alcohol for this pre-esterification step is methanol and for convenience the invention will be described with refeence to this preferred reagent. Comparatively mild reaction conditions are selected for this process, so that transesterification of triglycerides takes place only to a limited extent, if at all.

The ratio between triglyceride starting material and methanol is best selected so that, on the one hand, a distinct molar excess of methanol is provided relative to the free fatty acid content to be esterified, while, on the other hand, a clean separation occurs between the oil phase and the methanol phase at the end of the reaction. Generally, to achieve this result, from about 10 to 50 percent by volume of methanol is normally used, based on the volume of trigyceride starting material. Preferred amounts for this pre-esterification reaction are about 15 to 40 percent by volume with the most preferred being about 20 percent by volume. These ratios roughly correspond to molar ratios of methanol (lower monoalcohol) to free fatty acid of about 10:1 to 50:1 depending on the nature and acid number of the triglyceride starting material. Preferably a molar ratio of about 20:1 to 25:1 is employed.

Larger quantities of methanol have a positive effect upon the velocity and completeness of the esterification of the free fatty acids. Even though the solubility of methanol in natural triglycerides, which is constant for a given reaction temperature, is limited, it has been found that to a certain extent an increase in the quantity of methanol used produces more rapid and more complete esterification of the free fatty acids. With the economy of the process in mind, however, it is generally advisable to impose an upper limit, as above indicated, on the quantity of methanol used in the pre-esterification reaction, because recovery of the excess alcohol can be a significant cost factor.

The pre-esterification step generally is carried out at substantially atmospheric pressure. The term "substantially atmospheric pressure" as used herein is intended to include slight positive pressures which may be advantageous, e.g., up to about 5 bar. At these conditions special pressure reactors are not required. The reaction temperature can be varied between about the boiling point of the monoalcohol down to about 10° C. below the boiling point and to a certain extent is a function of pressure. For example, when methanol is used, the reaction temperature should be within the range of about 55° to 65° C.

In this pre-esterification step, the reactants are contacted in the presence of a solid acidic catalyst at a suitable reaction temperature until the acid number of the oil phase has fallen to the required level. The reactant mixture can be contacted with the catalyst using any of a wide variety of known solid-liquid contacting techniques. In order to achieve optimal results in subsequent transesterification of the natural fat or oil, the acid number of the triglyceride starting material is geneally reduced to a value of below about 1. For example, where coconut oil is used, the acid number of approximately 10 in the crude oil can be reduced to a value below about 1 using the esterification process of this invention.

Preferred solid acid catalysts for use in the present invention are strongly acidic ion (cation) exchange resins containing the residues of strong acids in their free form bound to a polymer matrix. The solid acid catalysts of this inention do not dissolve in the reaction mixture and thus readily can be separated from the reaction product by a simple and straightforward phase separation using any of a wide variety of well-known equipment and procedures. Ion exchange resins containing free sulfonic acid groups as the ion-exchanging moity, for example bound to a polystyrene copolymer, are particularly well known to those skilled in the art, as are those containing carboxylic acid groups. As recognized by those skilled in the art, ion exchange resins of the type are commercially available from a variety of sources in various forms, e.g., as small beads, and under various names, such as Amberlite ® from the Rohm and Haas Co., Permutit ® and Dowex ® from the Dow Chemical Company and Lewatit ® from Bayer AG. Macroporous resins which facilitate intensive contact between the oil phase and the heterogeneous solid catalyst phase are particularly suitable for use in connection with the present invention. informative literature references to suitable ion exchange resins containing residues of strong acids as the ion exchanging group, particularly sulfonic acid residues, can' be found, for example, in Ullmanns Enzyklopadie der technischen Chemie, 3rd Edition, Vol. 8, Munich-Berlin 1957, pages 806 to 817, cf. in particular Table 3 on page 816.

Particularly suitable acidic ion exchange resins for use as a solid heterogeneous catalyst in accordance with the present invention are strongly acidic, macroporous ion exchange resins marketed, for example, under the trademark Lewatit ® by Bayer AG, more particularly the types SPC 118 BG, SPC 118, SPC 108 BGT and SPC 108 useable in anhydrous and non-polar media.

In the process of the present invention, these heterogeneous solid catalysts may be used as a fixed bed through which the triglyceride mixture containing free fatty acids to be treated is passed. For example, crude oil at a temperature of approximately 60° to 65° C. may be pumped with methanol through a fixed-bed column consisting of the acid catalyst ion exchange resin.

The alcohol and oil components may be circulated in countercurrent or cocurrent fashion through the fixed bed of the acidic ion exchange resin. Furthermore, the heterogeneous solid catalysts also may be used in the form of a moving mass, for example in the form of a moving bed or fluidized bed, as long as the reliable separation of the solid catalyst from the liquid phase reaction mixture by a subsequent separation step is guaranteed. In any event, after the acid number of the triglyceride mixture has been lowered to the desired extent, the fat or oil containing the esterified fatty acids is separately recovered from the solid acidic esterification catalyst, e.g., using any of a wide variety of solids-liquid separation equipment and procedures such as filtering.

In preferred practice wherein the triglyceride mixture is passed, without recirculation, through a bed of ion exchange resin, the catalyst volume, based on the oil throughput, amounts to between about 1 and 10 liters of resin per liter of crude oil per hour and, more particularly, to between about 1.5 and 7.5 liters of resin per liter of crude oil per hour. This corresponds to contacting times between about 1 and 10 hours and preferably between about 1.5 and 7.5 hours, which also can be used to design recirculating and batch type arrangements.

In practice, the pre-esterification may be carried out, for example, by passing the liquid stream to be treated through a single column or through two serially arranged ion exchange columns heated to the reaction temperature. The liquid phase preferably flows upwardly through the ion exchange columns. Any gaseous components formed (air bubbles or evaporated alcohol) pass through the catalyst bed and are condensed or vented at the head of the column. Screens at the head of the column prevent removal of the ion exchange resin. Any sludge or slime present in the crude oil separates from the esterified oil. The product stream is freed from its water content and from any free alcohol residue as described below. A portion of the purified, dried, esterified oil may be recycled as diluent to the preliminary esterification stage.

In order to remove water formed during esterification which adversely affects subsequent transesterification of the triglycerides in the oil phase to their alkyl, e.g., methyl, esters, the reaction mixture separated from the solid acid catalyst is dried before being partly recycled or further processed. For example, the oil phase may be passed through a falling-film evaporator where water and residual methanol evaporate into the vapor phase. The water and methanol can be recovered from the process by condensation. By rectifying the recovered alcohol/water mixture, the alcohol component can be recycled to the pre-esterification process. The reaction mixture also may be dried by other methods known to those skilled in the art and the present invention is not to be limited to any particular drying technique. For example, the liquid mixture separated from the solid acid catalyst may be passed over a drying agent, such as a molecular sieve, whereby water of reaction is removed from the hydrocarbon mixture by adsorption.

To improve both the fluid flow and mass transfer between the triglycerides and alcohol of the reation mixture and the heterogeneous solid acid catalyst, it is useful to add a miscible diluent to the triglyceride/alcohol mixture. According to the present invention, a particularly suitable diluent is a recycled portion of the esterified reaction mixture having a reduced level of free fatty acids, e.g., having an acid number below about 1, or a recycled portion of the fatty acid aklyl ester recovered from subsequent transesterification of the triglyceride mixture. The diluent is added to the triglyceride mixture before it contacts the solid acid catalyst. The diluent may be added, for example, in a quantity of from about 25 to 500% by volume of the starting triglyceride mixture and, more particularly, in a quantity of from about 50 to 200% by volume.

Although the present invention is not to be limited to any particular procedure for transesterifying the pre-esterified triglyceride mixture, the anhydrous triglycerides recovered from the process of the present invention preferably are subjected to atmospheric alkalicatalyzed transesterification at a reaction temperature in the range of from about 25° to 100° C. in a known manner with a lower monoalcohol, e.g., an alkanol having 1 to 4 carbon atoms. The reaction is conducted at substantially atmospheric pressure and it is preferred to carry out the reaction at the reflux temperature of the alcohol employed, e.g., for methanol, at about 65° C. Reaction times between about 10 to 60 minutes being typical. Preferred is the same monoalcohol used in the pre-esterification step of the present invention. The most preferred monoalcohol for both steps is methanol and for convenience the transesterification step will be described briefly with reference thereto.

The transesterification reaction can be carried out batchwise or continuously in any of the many known non-pressurized reaction systems. In general, the methanol is used in a 50% to 150% excess over the stoichiometric quantity required for the transesterification reactions. The transesterification reaction should be carried out with substantially anhydrous methanol. Suitable catalysts for transesterification inlcude alkali metal hydroxides, particularly sodium and potassium hydroxide, and alkali metal alcoholates, particularly sodium methylate. In measuring the quantity of catalyst, it is essential to take into account any residue of free fatty acids still present in the triglyceride in question. Over and above the quantity required to neutralize any free fatty acids, the catalysts are used in quantities of from about 0.05 to 0.2 percent by weight based on the triglycerides. Preferred are catalyst quantities of from about 0.1 to 0.2 percent by weight, with about 0.15 percent by weight being most preferred.

The following examples are presented to illustrate further the present invention and are not intended to limit its scope which is defined by the appended claims.

EXAMPLES

EXAMPLE 1

Preliminary esterification was carried out continuously in two serially arranged 100 mm diameter ion exchange columns, each filled with 3.5 liters of Lewatit ® SPC 118 BG ion exchange resin. Both columns were heated to a temperature of 64° C. by a jacket heating system.

A reaction mixture comprising 0.2 l/h of methanol, 1 l/h of unpurified coconut oil (acid number 10) and 0.98 l/h of recycled product was preheated to the reaction temperature of 64° C. and pumped upwardly through the columns. In order to retun the recycled product in anhydrous form, the product stream issuing from the ion exchange resin columns was passed through a falling-film evaporator which, as a recirculation evaporator, required a liquid phase temperature of about 120° C. at ambient presure. The anhydrous oil freed from excess methanol had an acid number of 0.55 and a water content of 0.08% by weight.

Sludge and slime present in the crude oil was separated in a separator. A component stream of 0.98 /hr of the product continuously pre-esterified in this way was returned as the recycle stream. The remainder of the product stream was delivered to a transesterification reactor.

EXAMPLE 2

4.4 l of Lewatit® SPC 118 BG ion exchange resin were filled into a heatable tube having an internal diameter of 30 cm. A reaction mixture comprising 3 l/h of unpurified coconut oil (acid number 10) and 0.6 l/h of methanol was heated in a heat exchanger to a temperature of 64° C.

After flowing once through the fixed bed, itself heated to a temperature of 62° C., the reaction mixture had an acid number of 0.56.

EXAMPLE 3

The ion exchange resins Lewatit® SPS 108, SPC 118 and SPC 118 BG wee comparison tested. A mixture of 90 ml of methanol, 1800 ml of coconut oil, and 460 ml of its methyl ester wee pumped at a circulation rate of 25 l/h through a heated column (64° C.) filled with 517 g of resin.

At the beginning of the reaction, the mixture contained free fatty acids and had an acid number of 3.2.

After recirculation for 2 hours, the mixtures discharged from the column had acid numbers of 0.91, 1.15 and 0.89, respectively. After recirculation for 6 hours, the acid numbers of the mixtures were 0.32, 0.42 and 0.41, respectively.

Although certain embodiments of the present invntion have been described in detail, it will be appreciated that other embodiments are contemplated along with modification of the disclosed features, as being within the scope of the invention, which is defined in the appended claims.

What is claimed is:

1. A continuous process for the pre-esterification of a fat or oil to reduce the free fatty acid content thereof prior to transesterification comprising:

(a) passing a crude fat or oil of vegetable or animal origin in admixture with methanol in a molar ratio of methanol to the free fatty acid content of the fat or oil of from about 10:1 to 50:1, at a temperature of from about 55° C. to 65° C., over a fixed bed, heterogeneous pre-esterification catalyst which is a solid, acidic, anion exchange resin comprising a polymer matrix having bound thereto free sulfonic acid groups, to pre-esterify free fattya cid and reduce the acid value of the fat or oil to below about 1;
   (b) separating the pre-esterified fat or oil from the fixed bed catalyst and passing the separated fat or oil through evaporator means for evaporating water and residueal methanol from the oil phase into the vapor phase to purify and dry the pre-esterified fat or oil; and
   (c) separately recovering purified, dired, pre-esterified fat or oil with an acid value below about 1, and methanol.

2. The process of claim 1 wherein said fat or oil is diluted with a fat or oil having a reduced level of free fatty acids prior to esterification.

3. The process of claim 1 wherein said fat or oil is diluted with a fatty acid aklyl ester prior to esterification.

4. The process of claim 2 wherein said fat or oil is diluted with between about 25 to 500% by volume, based on said fat or oil, of said fat or oil having a reduced level of free fatty acids.

5. The process of claim 4 wherein said diluent comprises beween about 50 to 200% by volume.

6. The process of claim 3 wherein said fat or oil is diluted with between about 25 to 500% by volume, based on said fat or oil, of said fatty acid alkyl ester.

7. The process of claim 6 wherein said diluent comprises between about 50 to 200% by volume.

8. The process of claim 1, wherein the evaporator means comprises a falling-film evaporator.

9. The process of claim 1, wherein the catalyst volume, based on the oil throughput, amounts to between about 1 to 10 liters of resin per liter of crude fat or oil per hour.

10. The process of claim 9, wherein the catalyst volume, based on the oil throughput, is from 1.5 to 7.5 liters of resin per liter of crude fat or oil per hour.

11. The process of claim 1, wherein the molar ratio of methanol to free fatty acid is from about 20:1 to 25:1.

* * * * *